United States Patent
Saitou et al.

(10) Patent No.: US 8,212,067 B2
(45) Date of Patent: Jul. 3, 2012

(54) METHOD FOR RECOVERING (METH)ACRYLONITRILE

(75) Inventors: Shigeru Saitou, Kurashiki (JP); Takayoshi Miyake, Kurashiki (JP)

(73) Assignee: Dia-Nitrix Co., Ltd., Tokyo (JP)

( * ) Notice: Subject to any disclaimer, the term of this patent is extended or adjusted under 35 U.S.C. 154(b) by 321 days.

(21) Appl. No.: 12/721,103

(22) Filed: Mar. 10, 2010

(65) Prior Publication Data
    US 2010/0256410 A1    Oct. 7, 2010

(30) Foreign Application Priority Data
    Apr. 7, 2009   (JP) ................................. 2009-093073

(51) Int. Cl.
    *C07C 253/34*    (2006.01)
(52) U.S. Cl. ....................................... 558/463
(58) Field of Classification Search ............... 558/463
    See application file for complete search history.

(56) References Cited

FOREIGN PATENT DOCUMENTS

| JP | 55-104243 | 8/1980 |
|----|-----------|--------|
| JP | 2002-518353 | 6/2002 |
| WO | WO 99/65583 | * 12/1999 |

* cited by examiner

*Primary Examiner* — Joseph Kosack
(74) *Attorney, Agent, or Firm* — Oblon, Spivak, McClelland, Maier & Neustadt, L.L.P.

(57) ABSTRACT

An increase in the differential pressure in the distillation tower for the recovery of (meth)acrylonitrile is suppressed, and a stable and efficient operation is performed over a long time. A method for recovering (meth)acrylonitrile from a mixture containing (meth)acrylonitrile, acetonitrile and unsaturated compounds, in which the mixture is introduced into a distillation tower, distillation is performed under the conditions that the overhead liquid of the distillation tower contains (meth)acrylonitrile, acetonitrile is drawn out from the bottom and/or a side stream of the distillation tower, and a liquid containing the unsaturated compounds is drawn out from a site higher in position than the position of drawing acetonitrile.

4 Claims, 4 Drawing Sheets

METHOD FOR RECOVERING (METH)ACRYLONITRILE

BACKGROUND OF THE INVENTION

1. Field of the Invention

The present invention relates to a method for recovering (meth)acrylonitrile, and more particularly, to a method for recovering (meth)acrylonitrile by separating acetonitrile and hydrogen cyanide, which are side products, from a reaction product obtainable from the production process for (meth) acrylonitrile through distillation in a distillation tower, in which method stable and efficient purification by distillation is performed over a long time by suppressing an increase in the differential pressure in the distillation tower.

As used herein, the term (meth)acrylonitrile refers to acrylonitrile or methacrylonitrile.

Priority is claimed on Japanese Patent Application No. 2009-093073, filed Apr. 7, 2009, the content of which is incorporated herein by reference.

2. Description of Related Art

Generally, in the production process for acrylonitrile or methacrylonitrile, an ammoxidation reaction is used.

In this production process for (meth)acrylonitrile based on ammoxidation, first, a hydrocarbon such as propylene or isobutene, ammonia and an oxygen-containing gas such as air are introduced into a reactor and are subjected to an ammoxidation reaction in the presence of a catalyst. If acrylonitrile is to be produced, propylene is used as the raw material hydrocarbon, and if methacrylonitrile is to be produced, isobutene is used as the raw material hydrocarbon. In this ammoxidation reaction, acetonitrile and hydrogen cyanide are generated as side products, together with the target product (meth)acrylonitrile. Thus, the ammoxidation reaction gas obtained from the reactor contains not only (meth)acrylonitrile but also acetonitrile and hydrogen cyanide, and also contains unreacted ammonia or other lightweight gases.

Therefore, first, the obtained ammoxidation reaction gas is sent to an ammonia absorption tower to add sulfuric acid thereto, and ammonia is removed from ammonium sulfate. The separated gas having ammonia removed in the ammonia absorption tower is subsequently sent to a (meth)acrylonitrile absorption tower, and (meth)acrylonitrile, hydrogen cyanide and the like are absorbed using absorption water that is supplied from the top of the tower. The obtained bottoms liquid is sent to a (meth)acrylonitrile recovery tower. In this (meth) acrylonitrile recovery tower, acetonitrile is separated to recover (meth)acrylonitrile, and the (meth)acrylonitrile obtained from the (meth)acrylonitrile recovery tower is further purified in a purification tower, to thereby obtain (meth) acrylonitrile as a product.

There have been hitherto suggested various suggestions for the purpose of enhancing the recovery efficiency for (meth) acrylonitrile at the (meth)acrylonitrile recovery tower in this production process for (meth)acrylonitrile. For example, JP-T-2002-518353 suggests a method of separating by distillation the overhead stream enriched with acrylonitrile at the recovery tower, a side stream composed of water with less foreign materials, and a bottom stream containing organic impurities.

JP-A-55-104243 also suggests a method of separating by distillation a distillate fraction containing (meth)acrylonitrile, hydrogen cyanide and a small amount of water from the overhead of a distillation tower, acetonitrile from a middle tray, and water from the bottom, respectively.

SUMMARY OF THE INVENTION

In a conventional (meth)acrylonitrile recovery tower, the differential pressure in the tower increases as time elapses, and it is difficult to maintain long-term stable operation.

This increase in the differential pressure is due to the accumulation of blocking materials in the tower. For this reason, when the increase in the differential pressure causes an impediment in the operation, or when such an impediment is predicted, a process of stopping the operation and removing the blocking materials in the tower is required. Then, there are required purchases and costs for this process, and there is also a problem of a decrease in the production efficiency due to the stoppage of operation.

The invention was made to solve those problems of the related art, and it is an object of the invention to provide a method for recovering (meth)acrylonitrile, which makes it possible to conduct stable and efficient operations over a long time by suppressing an increase in the differential pressure of a distillation tower for the recovery of (meth)acrylonitrile.

The present inventors conducted a thorough investigation to solve the problems, and as a result, they found that the cause of an increase in the differential pressure in the tower of a conventional (meth)acrylonitrile recovery tower is that a certain kind of olefinic unsaturated compound causing polymerization stays in the middle trays of the distillation tower, this is concentrated and polymerizes in the tower as time elapses, and this polymerization product becomes a blocking material in the tower to cause an increase in the differential pressure in the tower; and therefore, an increase in the differential pressure in the tower can be prevented by drawing this unsaturated compound. They also found that it is possible to draw out this unsaturated compound at a site which is higher than the draw position for acetonitrile at the recovery tower.

Conventionally, acetonitrile has been drawn at a middle tray of a (meth)acrylonitrile recovery tower. However, what was not completely realized concerned the presence of certain kinds of unsaturated compounds causing polymerization in the tower, and the drawing of these unsaturated compounds from a site higher than the drawing site for acetonitrile, that is, what these unsaturated compounds are, that these compounds become a cause of the blocking materials increasing the differential pressure, or that these unsaturated compounds are concentrated at a site higher than the drawing site for acetonitrile. These matters have been elucidated for the first time by the present inventors.

The present invention was made based on such findings, and the gist lies in the following.

(1) A method for recovering (meth)acrylonitrile from a mixture containing (meth)acrylonitrile, acetonitrile and unsaturated compounds other than those, wherein the mixture is introduced into a distillation tower, distillation is performed under the conditions that the overhead stream liquid of the distillation tower contains (meth)acrylonitrile, acetonitrile is drawn out from the bottoms and/or a side stream of the distillation tower, and a liquid containing the unsaturated compounds is drawn out from a site higher than the drawing site for acetonitrile.

(2) The method for recovering (meth)acrylonitrile according to (1), wherein the liquid containing the unsaturated compounds is drawn out at a ratio of 0.04 wt % or more with respect to the amount of the mixture introduced into the distillation tower.

(3) The method for recovering (meth)acrylonitrile according to (1) or (2), wherein the unsaturated compounds are dienes.

(4) The method for recovering (meth)acrylonitrile according to (3), wherein the unsaturated compounds are butadienes, and the concentration of the unsaturated compounds in the liquid containing the unsaturated compounds is 0.01 wt % or more.

According to the invention, when unsaturated compounds which cause blocking in the tower are drawn out efficiently from the distillation tower, these unsaturated compounds are prevented from being concentrated in the tower, and the production of blocking materials due to polymerization of these unsaturated compounds and a consequent increase in the differential pressure in the tower are reliably prevented. Thus, it is possible to continuously carry out the operation stably and efficiently over a long time.

DETAILED DESCRIPTION OF THE INVENTION

Figure 1:
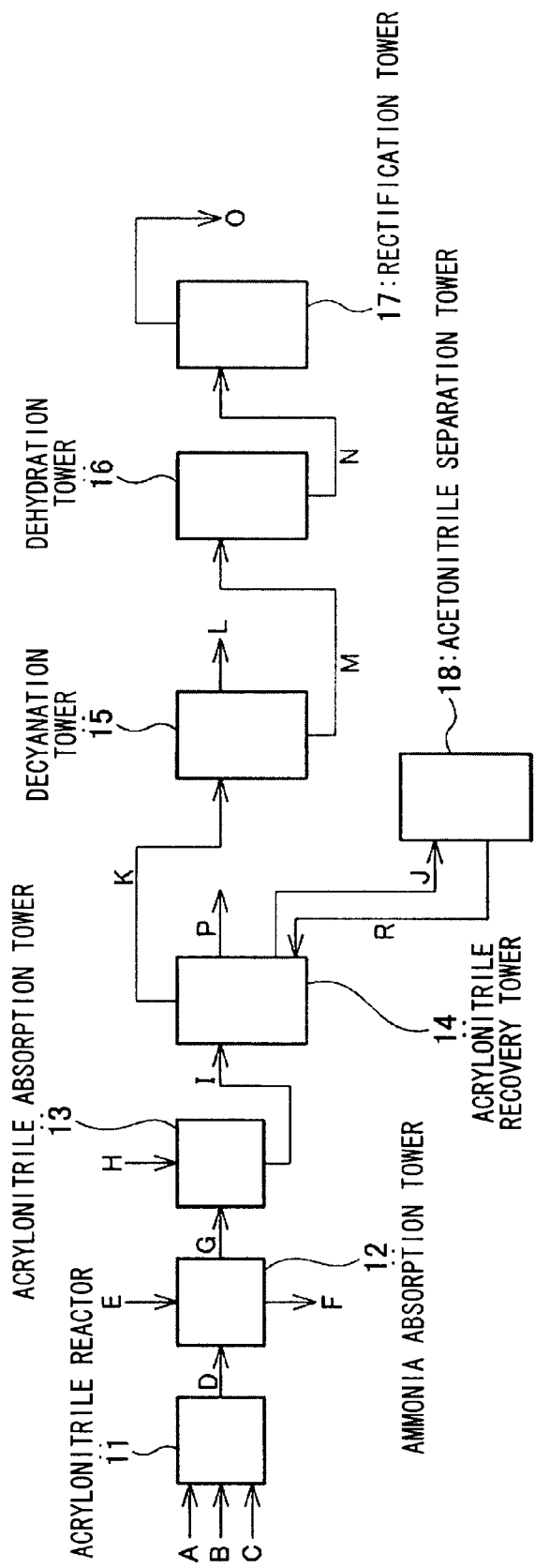
FIG. 1 is a flow diagram for the acrylonitrile production process according to an embodiment of the method for recovering (meth)acrylonitrile of the invention.

Hereinafter, embodiments of the invention will be described in detail, but the explanation of the constitution requirements described below is an example (representative example) of the embodiments of the invention. The invention is not intended to be specified by these contents, so long as the contents are within the scope of the gist.

The method for recovering (meth)acrylonitrile of the invention is a method of recovering (meth)acrylonitrile from a mixture containing (meth)acrylonitrile, acetonitrile, and unsaturated compounds other than those (that is, other than (meth)acrylonitrile and acetonitrile), wherein the mixture is introduced into a distillation tower, distillation is performed under the conditions that the overhead stream liquid of the distillation tower contains (meth)acrylonitrile, acetonitrile is drawn out from the bottom and/or a side stream of the distillation tower, and a liquid containing the unsaturated compounds is drawn out from a site higher than the drawing site for acetonitrile.

That is, according to the invention, a reaction product sent from a reaction process and containing (meth)acrylonitrile, acetonitrile and unsaturated compounds other than those, is introduced into a distillation tower as a (meth)acrylonitrile recovery tower, and distillation is performed in this distillation tower, to thereby draw out a (meth)acrylonitrile-containing distillate fraction from the overhead, and at the same time, to draw out acetonitrile from the bottom and/or a side stream, while a liquid containing the unsaturated compounds is drawn out at a site higher than the drawing site for this acetonitrile (hereinafter, this site may be referred to as "unsaturated compound drawing unit").

The unsaturated compounds drawn out from this unsaturated compound drawing unit are dienes, such as mainly butadienes (derivatives of butadiene, for example, cyanobutadiene). The component other than the unsaturated compounds in the liquid drawn from the unsaturated compound drawing unit is mostly water. This drawn liquid is discharged out of the system, and is supplied to waste water treatment.

According to the embodiment of the invention, it is preferable to adjust the position of the unsaturated compound drawing unit or the distillation conditions such that the concentration of the unsaturated compounds which cause a blocking material in the tower, in the liquid drawn from the unsaturated compound drawing unit is 0.01 wt % or more, particularly 0.05 wt % or more, and especially 0.10 wt % or more. Furthermore, since the unsaturated compounds are concentrated at a site higher than the acetonitrile drawing site, drawing from this site is effective in preventing an increase in the differential pressure in the tower. It is more preferable if the concentration of the unsaturated compounds in the drawn liquid is higher, but this concentration of the unsaturated compound is usually 0.20 wt % or less even at the concentrated site.

In regard to the drawn amount of the unsaturated compounds which cause a blocking material in the tower, the drawn amount of the liquid containing the unsaturated compounds from the unsaturated compound drawing unit is preferably adjusted to 0.04 wt % or more based on the amount of the mixture to be introduced into the distillation tower. As the amount of drawn liquid becomes larger, generation of the polymerization product resulting from the concentration of the unsaturated compounds in the tower can be prevented. However, if the amount is excessively large, the waste water cost is increased excessively, and it is economically disadvantageous. Therefore, the amount of liquid drawn from the unsaturated compound drawing unit is preferably adjusted to 0.04 wt % or more, particularly 0.10 wt % or more, and to 0.40 wt % or less, based on the amount of the mixture to be introduced into the distillation tower.

The unsaturated compound drawing unit is not particularly limited, so long as it is at a higher position than the acetonitrile drawing site and is at a lateral side of the distillation tower at a position lower than the top of the tower, but it is preferable to draw out from a site where the concentration of the unsaturated compounds which cause blocking in the tower is high. Usually, in the distillation tower for the recovery of (meth) acrylonitrile, since the liquid to be distilled (that is, the mixture containing (meth)acrylonitrile, acetonitrile and unsaturated compounds other than those; generally, the bottoms liquid from the (meth)acrylonitrile absorption tower, containing (meth)acrylonitrile, hydrogen cyanide and the like) is introduced to a lateral side of the distillation tower, it is preferable that the unsaturated compound drawing unit be at a position lower than this site of introduction.

The drawing of the unsaturated compounds may be carried out by drawing a side stream of the distillation tower and analyzing the content of the unsaturated compounds in accordance with the distillation conditions for the distillation tower, so that the liquid containing the unsaturated compounds is drawn out from a site where this content of the unsaturated compounds is the highest. However, it is preferable that the unsaturated compound drawing unit be, for example, at a position of $1/4$ to $2/3$ of the total tower height from the bottom of the distillation tower in which the site for introduction of the liquid to be distilled and the site for drawing of the product have been set up as follows, and be at a position higher than the site for drawing of acetonitrile by about $1/50$ to $1/2$ of the total tower height as shown below, and a position lower than the site for introduction of the liquid to be distilled by about 1/50 to 2/3 of the total tower height as shown below:

Drawing of overhead liquid containing (meth)acrylonitrile and water: Top of the tower Drawing of bottoms liquid composed mainly of water: Bottom of the tower Introduction of liquid to be distilled: Position of 1/2 to 1/1 of the tower height from the bottom of the tower (provided that the top of the tower is excluded)

Drawing of acetonitrile: Position of 1/50 to 1/2 of the tower height from the bottom of the tower The method for recovering (meth)acrylonitrile of the present invention can employ the distillation method or distillation conditions for conventional (meth)acrylonitrile recovery towers, except that the recovery is achieved at a site higher in position than the site for drawing of acetonitrile in the distillation tower as a (meth)acrylonitrile recovery tower in the conventional (meth)acrylonitrile production process, and that drawing of a liquid containing the unsaturated compounds causing blocking in the tower is performed.

Hereinafter, embodiments of the invention will be described with reference to FIGS. 1 to 3 which exemplify the case of applying the method for recovering (meth)acrylonitrile of the invention to the production process for acrylonitrile. However, the method for recovering (meth)acrylonitrile of the invention is not to be limited to any of the embodiments of FIGS. 1 to 3. Furthermore, the method of the invention is not limited to the recovery of acrylonitrile, and can be applied similarly to the recovery of methacrylonitrile.

[Embodiment 1 (FIG. 1)]

FIG. 1 is a flow diagram showing the production process for acrylonitrile, and in FIG. 1, a hydrocarbon A such as propylene, ammonia B, and an oxygen-containing gas C such as air are sent to an acrylonitrile reactor 11, and are subjected to an ammoxidation reaction in this reactor 11 in the presence of a catalyst.

The reaction gas from the acrylonitrile reactor 11 is subsequently sent to an ammonia absorption tower 12 to have unreacted ammonia eliminated, and sulfuric acid E is added thereto, so that ammonia is eliminated as ammonium sulfate F.

The separated gas G from which ammonia has been eliminated at the ammonia absorption tower 12, is subsequently sent to an acrylonitrile absorption tower 13, and absorption water H supplied from the top of the tower absorbs acrylonitrile, hydrogen cyanide and the like. A bottoms liquid I containing these is sent to an acrylonitrile recovery tower 14.

In this acrylonitrile recovery tower (distillation tower according to the invention) 14, a mixed gas J containing hydrogen cyanide and acetonitrile is drawn out from a middle tray of the tower and is introduced into an acetonitrile separation tower 18. Water R is separated at the acetonitrile separation tower 18. The separated water R is returned to the recovery tower 14, and water separated. The residual fraction having the water content reduced is cooled and condensed by a heat exchanger, which is not illustrated, and is disposed of by incineration.

An overhead liquid K of the acetonitrile recovery tower 14 contains the target product acrylonitrile and hydrogen cyanide, and is sent to a decyanation tower 15. After hydrogen cyanide L is separated, a bottoms liquid M containing acrylonitrile is sent to a dehydration tower 16 and is dehydrated therein. A dehydrated bottoms liquid N from the dehydration tower 16 is further sent to a rectification tower 17 and purified, so that acrylonitrile O is obtained as a product.

According to the invention, in the acetonitrile recovery tower 14, a liquid P containing a lot of unsaturated compounds which are highly polymerizable is drawn out at a site higher in position than the site for drawing the mixed gas J containing acetonitrile.

This drawn liquid P is preferably drawn out from the acrylonitrile recovery tower 14 at the unsaturated compound concentration and amount of drawn liquid as described above, and is supplied to waste water treatment.

[Embodiment 2 (FIG. 2)]

Figure 2:
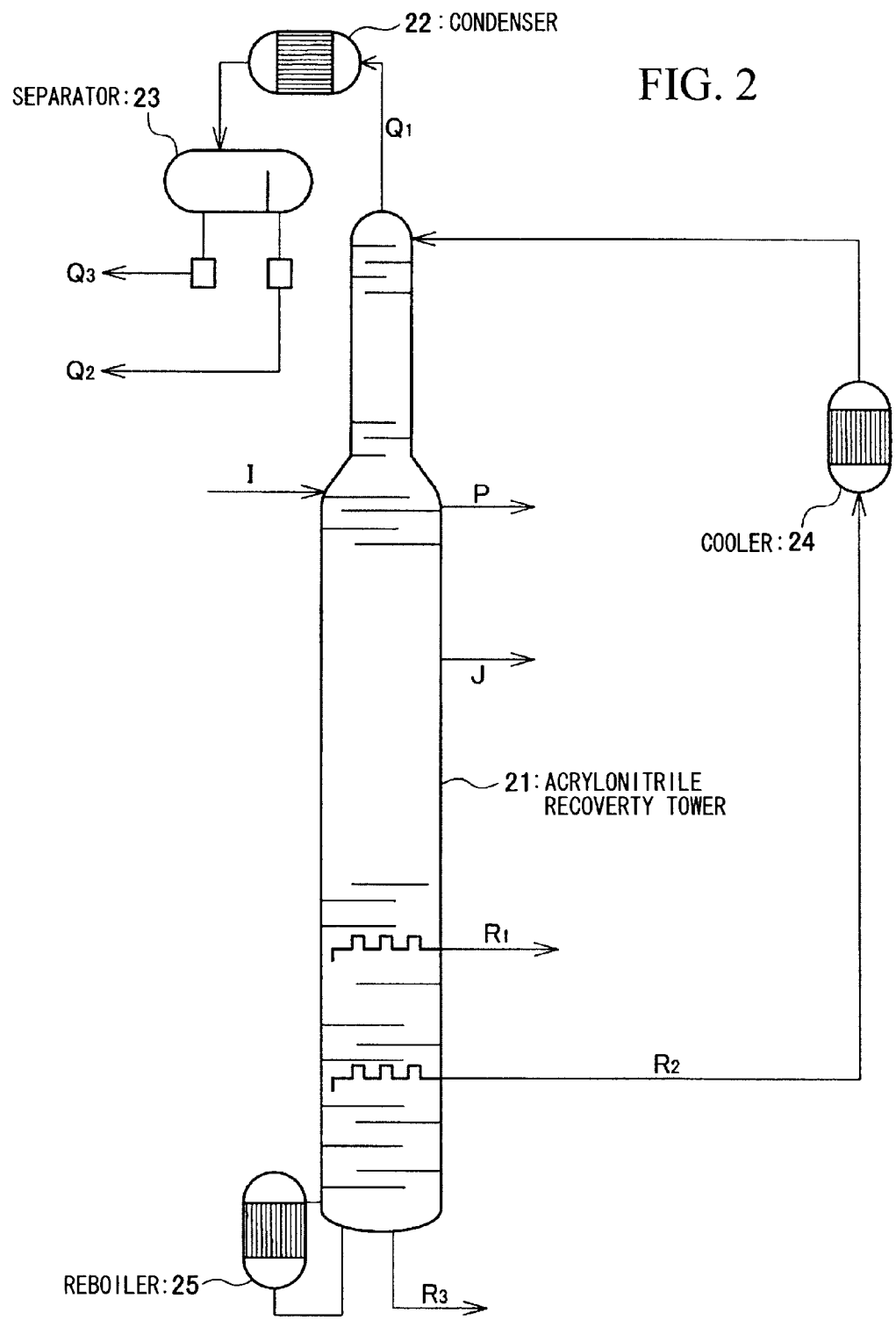
FIG. 2 is a schematic diagram of an acrylonitrile recovery tower according to another embodiment of the method for recovering (meth)acrylonitrile of the invention.

FIG. 2 is a schematic diagram showing a tray type acrylonitrile recovery tower (distillation tower related to the invention) 21, to which the bottoms liquid I containing acrylonitrile, hydrogen cyanide and acetonitrile obtained at an acrylonitrile absorption tower (for example, acrylonitrile absorption tower 13 in FIG. 1) is introduced.

In this acrylonitrile absorption tower 21, an overhead stream $Q_1$ containing water and acrylonitrile is obtained from the top of the tower, and this overhead stream $Q_1$ is sent to a separator 23 via a condenser 22 to be separated into an acrylonitrile stream $Q_2$, the target product, and a water stream $Q_3$.

Furthermore, a mixed gas J of hydrogen cyanide and acetonitrile is drawn out at a position of about 1/3 of the height from the bottom of the recovery tower 21. Furthermore, a side stream $R_1$ is drawn out from a position lower than the position of drawing this mixed gas J, and this side stream $R_1$ is recycled to the acrylonitrile absorption tower. A side stream $R_2$ is also drawn out from a position lower than the position of drawing this side stream $R_1$, and this side stream $R_2$ is cooled by a cooler 24 and then recycled to the top unit of the recovery tower 21. A bottom stream $R_3$ drawn out from the bottom of the top is disposed. Unit 25 is a reboiler.

According to the invention, in such an acrylonitrile recovery tower 21, a liquid P containing the unsaturated compounds which cause blocking in the tower in the tower is drawn out as a side stream (lateral stream) at a site higher in position than the site for drawing the mixed gas J containing acetonitrile and hydrogen cyanide.

This drawn liquid P is preferably drawn out from the acrylonitrile recovery tower 21 at the unsaturated compound concentration and the amount of drawn liquid as described above, and is supplied to waste water treatment.

For example, in the case where the bottoms liquid I containing about 8 wt % of acrylonitrile and about 0.8 wt % of hydrogen cyanide, which is sent from the acrylonitrile absorption tower, is separated by distillation in a tray type acrylonitrile recovery tower 21 having 95 trays in total, as in Example 1 that will be described later, the mixed gas J containing hydrogen cyanide and acetonitrile is drawn out at the $30^{th}$ tray position from the bottom of the tower, the side stream $R_1$ is drawn out at the $10^{th}$ tray position from the bottom of the tower, the side stream $R_2$ is drawn out at the first tray position from the bottom of the tower, and the drawn liquid P containing the unsaturated compounds which cause a blocking material in the tower is drawn at the $45^{th}$ tray position from the bottom of the tower, which is a site higher in position than the position of drawing the mixed gas J. Thus, concentration of the unsaturated compounds in the tower and an increase in the differential pressure in the tower due to polymerization can be effectively prevented.

[Embodiment 3 (FIG. 3)]

Figure 3:
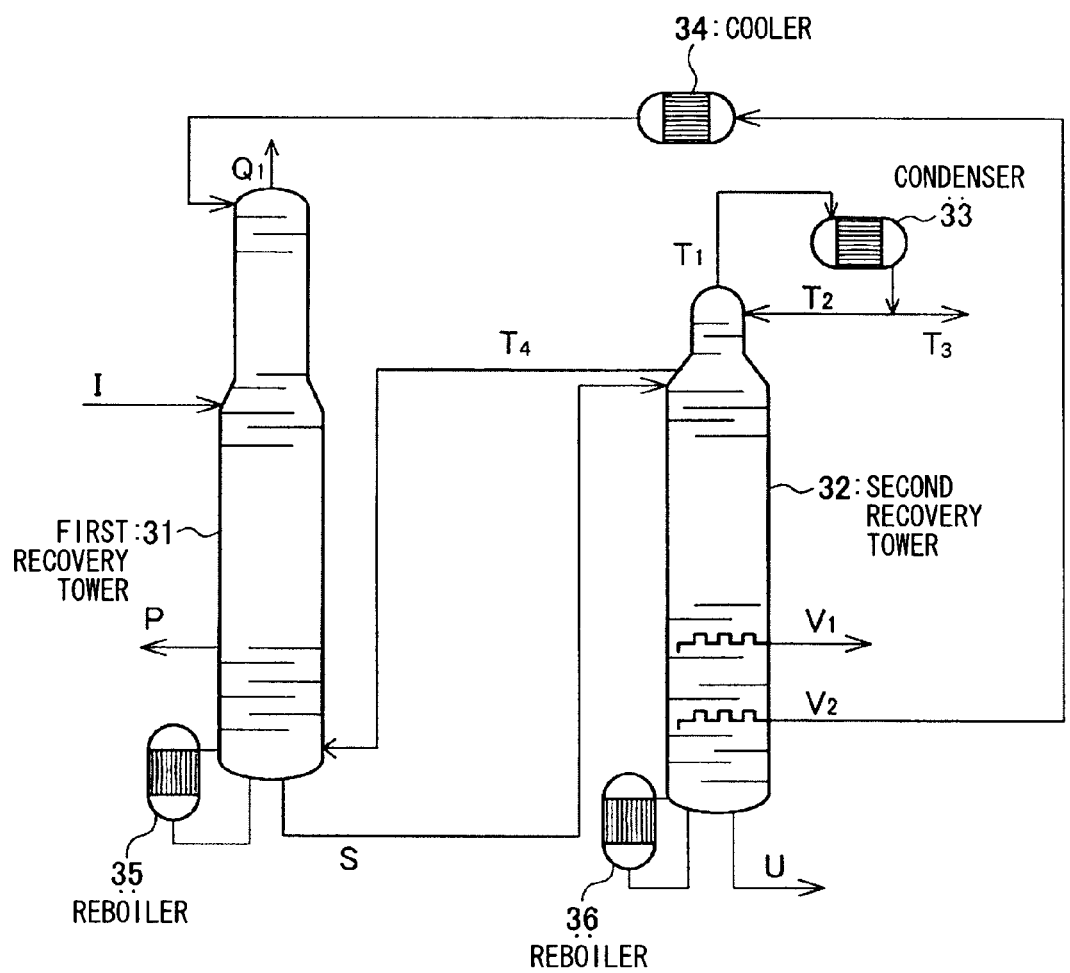
FIG. 3 is a schematic diagram of an acrylonitrile recovery tower according to another embodiment of the method for recovering (meth)acrylonitrile of the invention.

FIG. 3 is a schematic diagram showing an acrylonitrile recovery tower (distillation tower related to the invention) which performs recovery of acrylonitrile in a two-towered distillation tower having a first recovery tower 31 and a second recovery tower 32. The bottoms liquid I containing acrylonitrile, hydrogen cyanide and acetonitrile obtained from the acrylonitrile absorption tower (for example, the acrylonitrile absorption tower 13 in FIG. 1) is introduced into the first recovery tower 31.

In this first recovery tower 31, an overhead stream $Q_1$ containing water and acrylonitrile is obtained from the top of the tower, and this overhead stream $Q_1$ passes through a condenser that is not illustrated and is separated at a separator into an acrylonitrile stream, the target product, and a water stream, as in the case of the recovery tower 21 in FIG. 2.

From the bottom of the first recovery tower 31, a bottom stream S which contains water and various impurities and contains almost no acrylonitrile is drawn out, and this bottom stream S is sent to the second recovery tower 32.

The overhead stream $T_1$ of the second recovery tower 32 passes through a condenser 33, and a part thereof $T_2$ is recycled to the second recovery tower 32, while a residual part $T_3$ is disposed. The bottom stream U of the second recovery tower 32 is also disposed. Among the side streams $V_1$ and $V_2$ of the second recovery tower 32, the side stream $V_1$ of the upper tray side corresponds to the side stream $R_1$ of the recovery tower 21 of FIG. 2, and is recycled to the acrylonitrile absorption tower. The side stream $V_2$ of the lower tray side corresponds to the side stream $R_2$ of the recovery tower 21 of FIG. 2, and is cooled at a cooler 34 and then recycled to the top of the first recovery tower 31. Furthermore, a side stream $T_4$ at a high position near the top of the second recovery tower 32 is recycled to the lower part of the first recovery tower 31 so as to be used as a heat source for heating of the first recovery tower 31. Units 35 and 36 are reboilers.

According to the invention, among such acrylonitrile recovery towers, the first recovery tower 31 is a tower placed at a higher position than the second recovery tower 32, and from this first recovery tower 31, a liquid P containing the unsaturated compounds which cause a blocking material in the tower is drawn out as a side stream (lateral stream). That is, for example, in the case of using a first recovery tower 31 having 70 trays and a second recovery tower 32 having 30 trays, the $20^{th}$ tray from the bottom of this first recovery tower 31 corresponds to the $45^{th}$ tray of the acrylonitrile recovery tower 21 shown in FIG. 2, and thus the liquid P containing the unsaturated compounds can be drawn out from this site.

This drawn liquid P is preferably drawn out from the first recovery tower 31 at the unsaturated compound concentration and amount of drawn liquid as described above, and is supplied to waste water treatment.

As discussed above, according to the invention, a liquid containing unsaturated compounds which cause blocking in the tower is drawn out from a site higher than the site of drawing the liquid containing acetonitrile of the acrylonitrile recovery distillation tower, so that accumulation of the unsaturated compounds in the tower is prevented, and an increase in the differential pressure in the tower due to the polymerization product of the unsaturated compounds can be effectively prevented.

EXAMPLES

Hereinafter, the invention will be more specifically described with reference to Examples.

Example 1

Recovery of acrylonitrile was performed using the acrylonitrile recovery tower 21 shown in FIG. 2.

First, a reaction gas containing about 9 wt % of acrylonitrile from an acetonitrile reactor which is not illustrated, was sent to an ammonia absorption tower, and unreacted ammonia was eliminated. The resulting separated gas was absorbed into water at the acrylonitrile absorption tower.

Subsequently, a bottoms liquid (bottom stream) I obtained from the acrylonitrile absorption tower was supplied to the $58^{th}$ tray of an acrylonitrile recovery tower 21 having 95 trays (theoretical number of trays: 44), in which the diameter from the bottom of the tower to the $64^{th}$ tray was 3060 mm, and the diameter from the $65^{th}$ tray to the top of the tower was 2240 mm, at 80° C. and at a rate of 206 T/hr. The composition of this bottoms liquid I was 8 wt % of acrylonitrile, 0.1 wt % of acetonitrile, 0.8 wt % of hydrogen cyanide, 90.9 wt % of water, and 0.2 wt % of other impurities.

In this acrylonitrile recovery tower 21, liquid was drawn out respectively from the following sites. The site of drawing and temperature of the drawn liquid, and the amount of drawn liquid is presented in the following Table 1.

TABLE 1

| Site of drawing *1 | Amount of drawn liquid (T/hr) | Temperature of site of drawing (° C.) |
|---|---|---|
| $Q_1$ | Top of tower | 18.37 | 69 |
| P | 45 | 0.1 | 82 |
| J | 30 | 2 | 108 |
| $R_1$ | 10 | 165 | 113 |
| $R_2$ | 1 | 100 | 113 |
| $R_3$ | Bottom of tower | 25 | 115 |

The ratio of the amount of the liquid drawn from the $45^{th}$ tray (in terms of the theoretical number of trays, position of the $20^{th}$ tray from the bottom of the tower) from the bottom of the tower, to the amount of the liquid supplied to the $58^{th}$ tray from the bottom of the acrylonitrile recovery tower 21, was 0.049 wt %, and the concentration of butadienes in the liquid drawn from the $45^{th}$ tray from the bottom of the tower was 0.14 wt %. The operation was continued for 49 days under these conditions, but the pressure increase at the bottom of the recovery tower 21 was 0.023 kg/cm², and the operation could be stably achieved without requiring any temporary process of washing the recovery tower 21 or liquid drawing.

Figure 4:
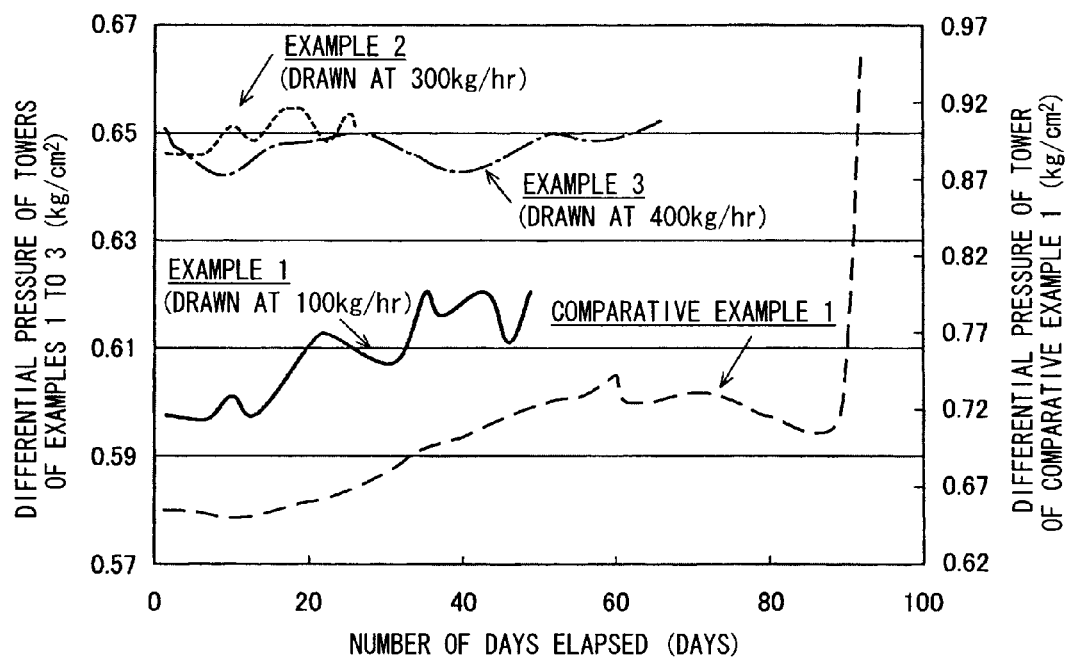
FIG. 4 is a graph showing the changes in the differential pressure in the tower over time in Examples 1 to 3 and Comparative Example 1.

The changes over time of the pressure at the bottom of the acrylonitrile recovery tower 21 during this operation period are presented in FIG. 4. The value of the "pressure increase at the bottom of the tower" is the difference between the pressure at the bottom of the tower on the $49^{th}$ day (0.6205 kg/cm²) from the initiation of operation of the distillation tower and the pressure at the bottom of the tower on the first day (0.5970 kg/cm²).

In the recovery tower, the pressure at the bottom of the tower corresponds to the differential pressure of the entire distillation tower, and therefore, an increase in the differential pressure of the entire tower can be understood from an increase in the pressure at the bottom of the tower.

Example 2

The operation was performed in the same manner as in Example 1, except that the amount of liquid drawn from the $45^{th}$ tray from the bottom of the tower was set to 0.3 T/hr (300 kg/hr). The ratio of the amount of liquid drawn from the $45^{th}$ tray from the bottom of the tower to the amount of liquid supplied to the $58^{th}$ tray from the bottom of the acrylonitrile recovery tower 21 was 0.145 wt %, and the concentration of butadienes in the liquid drawn from the $45^{th}$ tray from the bottom of the tower was 0.14 wt %.

As a result, the increase in the pressure at the bottom of the tower 26 days from the initiation of the operation was 0.0046 kg/cm², and the pressure increase was lower than that of Example 1. Furthermore, operation could be stably achieved without requiring any temporary process of washing the recovery tower 21 or liquid drawing.

The changes over time of the pressure at the bottom of the acrylonitrile recovery tower 21 during this operation period are presented in FIG. 4. The value of the "pressure increase at the bottom of the tower" is the difference between the pressure at the bottom of the tower on the 26$^{th}$ day (0.6509 kg/cm²) from the initiation of the operation of the distillation tower and the pressure at the bottom of the tower on the first day (0.6463 kg/cm²).

Example 3

An operation was performed in the same manner as in Example 1, except that the amount of liquid drawn from the 45$^{th}$ tray from the bottom of the tower was set to 0.4 T/hr (400 kg/hr). The ratio of the amount of liquid drawn from the 45$^{th}$ tray from the bottom of the tower to the amount of liquid supplied to the 58$^{th}$ tray from the bottom of the acrylonitrile recovery tower 21 was 0.194 wt %, and the concentration of butadienes in the liquid drawn from the 45$^{th}$ tray from the bottom of the tower was 0.14 wt %.

As a result, the increase in the pressure at the bottom of the tower 66 days from the initiation of operation was 0.0015 kg/cm², and the pressure increase was lower than that of Example 1 or 2. Furthermore, operation could be stably achieved without requiring any temporary process of washing of the recovery tower 21 or liquid drawing. The changes over time of the pressure at the bottom of the acrylonitrile recovery tower 21 during this operation period are presented in FIG. 4. The value of the "pressure increase at the bottom of the tower" is the difference between the pressure at the bottom of the tower on the 66$^{th}$ day (0.6526 kg/cm²) from the initiation of operation of the distillation tower and the pressure at the bottom of the tower on the first day (0.6511 kg/cm²).

Comparative Example 1

Recovery of acrylonitrile was performed using the acrylonitrile recovery towers 31 and 32 shown in FIG. 3.

First, a reaction gas containing about 9 wt % of acrylonitrile from an acrylonitrile reactor which is not illustrated, was sent to an ammonia absorption tower, and unreacted ammonia was eliminated. The resulting separated gas was absorbed into water at the acrylonitrile absorption tower. Subsequently, a bottoms liquid (bottom stream) I obtained from the acrylonitrile absorption tower was supplied to the 39$^{th}$ tray of an acrylonitrile recovery tower 31 having 70 trays, in which the diameter from the bottom of the tower to the 39$^{th}$ tray was 1830 mm, and the diameter from the 40$^{th}$ tray to the top of the tower was 1520 mm, at 83° C. and at a rate of 65 T/hr. The composition of this bottoms liquid I was 8 wt % of acrylonitrile, 0.1 wt % of acetonitrile, 0.8 wt % of hydrogen cyanide, 90.9 wt % of water, and 0.2 wt % of other impurities.

In this acrylonitrile recovery tower 31, liquids were drawn out from the top of the tower at 67° C. and at a rate of 4.3 T/hr and from the bottom of the tower at 109° C. and at a rate of 101 T/hr. Operation was continued for 52 days under these conditions, but the pressure increase at the bottom of the recovery tower 31 was 0.071 kg/cm². Thus, liquid drawing was performed from the 20$^{th}$ tray from the bottom of the tower, and although the pressure increase stopped transiently, the pressure increased again after 40 days, so that operation could not be continued. Accordingly, it was necessary to stop the operation and to wash the inside of the tower. The value of the "pressure increase at the bottom of the tower" is the difference between the pressure at the bottom of the tower on the 52$^{nd}$ day (0.726 kg/cm²) from the initiation of operation of the distillation tower and the pressure at the bottom of the tower on the first day (0.655 kg/cm²).

The changes over time of the pressure at the bottom of the acrylonitrile recovery tower 21 during this operation period are presented in FIG. 4.

In the present Comparative Example, the blocking material in the tower recovered when the pressure increased so that the operation had to be stopped and washing was performed, was analyzed by IR (infrared absorption spectrum), and it was confirmed to be a polymerization product of unsaturated compounds (mainly butadienes).

Figure 5:
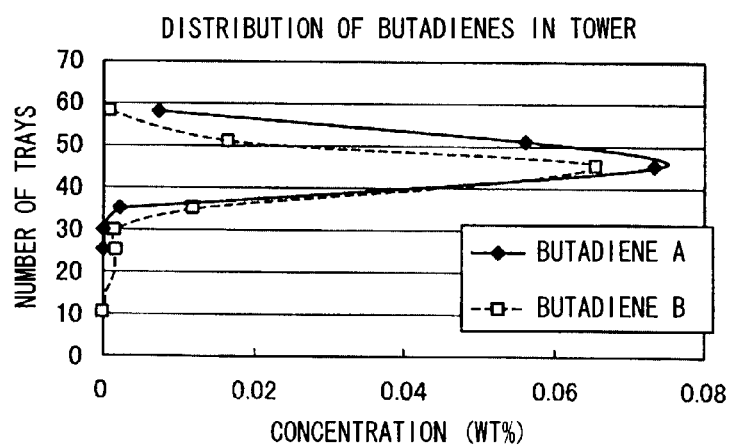
FIG. 5 is a graph showing the relationship between the concentration of butadienes in the liquid drawn from the acrylonitrile recovery tower (distillation tower) and the tray of drawing.

There, in order to examine the distribution of the unsaturated compounds which cause blocking in the tower, side streams were drawn out from various sites of the recovery tower, and the compositions were analyzed. As shown in Table 2 and FIG. 5, butadienes were contained in a large amount in the liquid drawn from near the 45$^{th}$ tray from the bottom of the tower, and thus it was confirmed that drawing out the unsaturated compounds from near this 45$^{th}$ tray is effective in preventing an increase in the differential pressure in the tower.

From the results of the Examples 1 to 3 and Comparative Example 1, it was confirmed that setting the amount of liquid drawn from near this 45$^{th}$ tray at 100 to 400 kg/hr (0.04 to 2.00 wt % with respect to the amount of liquid introduced into the recovery tower), and particularly at 400 kg/hr (0.194 wt % with respect to the amount of liquid introduced into the recovery tower), is suitable for long-term stable operation.

TABLE 2

| | Butadiene concentration in drawn liquid (wt %) Number of trays from bottom of tower | | | | | | |
|---|---|---|---|---|---|---|---|
| | 58 | 51 | 45 | 35 | 30 | 25 | 10 |
| Butadiene A *1 | 0.0073 | 0.056151 | 0.073362 | 0.002266 | 0 | 0 | 0 |
| Butadiene B *2 | 0.000941 | 0.01658 | 0.065628 | 0.011906 | 0.001643 | 0.001747 | 0 |

According to the invention, when unsaturated compounds which cause blocking in the tower are efficiently drawnout from the distillation tower, these unsaturated compounds are prevented from being concentrated in the tower, and production of a blocking material due to polymerization of these unsaturated compounds and an increase in the differential pressure in the tower resulting therefrom are reliably prevented, so that it is possible to utilize the tower by continuing the operation stably and efficiently over a long time.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A method for recovering (meth)acrylonitrile from a mixture containing (meth)acrylonitrile, acetonitrile and unsaturated compounds other than those, wherein the mixture is introduced into a distillation tower, distillation is performed under the conditions that the overhead stream liquid of the distillation tower contains (meth)acrylonitrile, acetonitrile is drawn out from the bottom and/or a side stream of the distillation tower, and a liquid containing the unsaturated compounds is drawn out from a site higher in position than the position of drawing acetonitrile.

2. The method for recovering (meth)acrylonitrile of claim 1, wherein the liquid containing the unsaturated compounds is drawn out at a ratio of 0.04 wt % or more with respect to the amount of the mixture introduced into the distillation tower.

3. The method for recovering (meth)acrylonitrile of claim 1 or 2, wherein the unsaturated compounds are dienes.

4. The method for recovering (meth)acrylonitrile of claim 3, wherein the unsaturated compounds are butadienes, and the concentration of the unsaturated compounds in the liquid containing the unsaturated compounds is 0.01 wt % or more.

* * * * *